US00PP20783P2

(12) United States Plant Patent
Junichi

(10) Patent No.: US PP20,783 P2
(45) Date of Patent: Feb. 23, 2010

(54) ***NASTURTIUM* PLANT NAMED 'AHIRU NO ASHI'**

(50) Latin Name: *Tropaeolium hybrida*
Varietal Denomination: Ahiru no Ashi

(75) Inventor: Nakata Junichi, Hirosaki (JP)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/291,392

(22) Filed: Nov. 7, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Nasturtium* plant named 'Ahiru no Ashi', characterized by its compact, upright and mounded to trailing plant habit; short internodes; dense and bushy growth habit; freely branching habit; freely flowering habit; and rich yellow-colored flowers with frilled margins.

1 Drawing Sheet

Botanical designation: *Tropaeolium hybrida.*
Cultivar denomination: 'Ahiru no Ashi'.

BACKGROUND OF THE INVENTION

The present invention relates to a new and distinct cultivar of *Nasturtium* plant, botanically known as *Tropaeolium hybrida* and hereinafter referred to by the name 'Ahiru no Ashi'.

The new *Nasturtium* plant is a naturally-occurring whole plant mutation of the *Tropaeolium hybrida* 'Whirlybird', not patented. The new *Nasturtium* was discovered and selected by the Inventor as a single flowering plant from within a population of plants of 'Whirlybird' in a controlled greenhouse environment in Aomori-ken, Japan in 2004.

Asexual reproduction of the new *Nasturtium* plant by terminal cuttings in Aomori-ken, Japan, since 2004, has shown that the unique features of this new *Nasturtium* plant are stable and reproduced true to type in successive generations.

SUMMARY OF THE INVENTION

Plants of the new *Nasturtium* have not been observed under all possible environmental conditions. The phenotype may vary somewhat with variations in environment such as temperature and light intensity without, however, any variance in genotype.

The following traits have been repeatedly observed and are determined to be the unique characteristics of 'Ahiru no Ashi'. These characteristics in combination distinguish 'Ahiru no Ashi' as a new and distinct cultivar of *Nasturtium:*

1. Compact, upright and mounded to trailing plant habit.
2. Short internodes; dense and bushy growth habit.
3. Freely branching habit.
4. Freely flowering habit.
5. Rich yellow-colored flowers with frilled margins.

Plants of the new *Nasturtium* can be compared to plants of the parent, 'Whirlybird'. Plants of the new *Nasturtium* differ from plants of 'Whirlybird' in the following characteristics:

1. Plants of the new *Nasturtium* have a detectable fragrance whereas plants of 'Whirlybird' do not have a detectable fragrance.

2. Flowers of plants of the new *Nasturtium* have fringed margins whereas flowers of plants of 'Whirlybird' do not have fringed margins.

Plants of the new *Nasturtium* can also be compared to plants of *Nasturtium splendens* 'Whirlybird Golden Yellow', not patented. Plants of the new *Nasturtium* differ from plants of 'Whirlybird Golden Yellow' in the following characteristics:

1. Plants of the new *Nasturtium* have a detectable fragrance whereas plants of 'Whirlybird Golden Yellow' do not have a detectable fragrance.
2. Flowers of plants of the new *Nasturtium* have fringed margins whereas flowers of plants of 'Whirlybird Golden Yellow' do not have fringed margins.

BRIEF DESCRIPTION OF THE PHOTOGRAPHS

The accompanying colored photographs illustrate the overall appearance of the new *Nasturtium* plant, showing the colors as true as it is reasonably possible to obtain in colored reproductions of this type. Colors in the photographs may differ slightly from the color values cited in the detailed botanical description which accurately describe the actual colors of the new *Nasturtium* plant.

The photograph at the bottom of the sheet comprises a side perspective view of a typical flowering plant of 'Ahiru no Ashi' grown in a container.

The photograph at the top of the sheet is a close-up view of typical flowers and flower buds of 'Ahiru no Ashi'.

DETAILED BOTANICAL DESCRIPTION

The aforementioned photographs and following observations, measurements and values describe plants grown in Bonsall, Calif., under commercial practice during the summer in a polyethylene-covered greenhouse. During the production of the plants, day temperatures ranged from 18° C. to 35° C. and night temperatures ranged from 13° C. to 24° C. Plants had been growing for eleven weeks when the description and photographs were taken. In the following description, color references are made to The Royal Horticultural Society Colour Chart, 2001 Edition, except where general terms of ordinary dictionary significance are used.

Botanical classification: *Tropaeolium hybrida* 'Ahiru no Ashi'.

Parentage: Naturally-occurring whole plant mutation of *Tropaeolium hybrida* 'Whirlybird', not patented.

Propagation:

*Type.*—By terminal cuttings.

*Time to initiate roots, summer.*—About three to six days at 32° C. to 35° C.

*Time to initiate roots, winter.*—About eight to ten days at 32° C. to 35° C.

*Time to produce a rooted young plant, summer.*—About four weeks at 32° C.

*Time to produce a rooted young plant, winter.*—About six weeks at 14° C.

*Root description.*—Fibrous, medium in thickness; white in color.

*Rooting habit.*—Freely branching; moderately dense.

Plant description:

*Plant habit.*—Compact, upright and mounding to trailing.

*Growth habit.*—Vigorous.

*Plant height.*—About 26 cm.

*Plant diameter.*—About 27 cm.

*Lateral branch description.*—Branching habit: Freely branching with about nine to ten primary lateral branches per plant. Length: About 44 cm. Diameter: About 4 mm. Internode length: About 1.1 cm to 3.3 cm. Strength: Strong; flexible. Texture: Smooth, glabrous. Color: Close to 145C.

Foliage description:

*Arrangement.*—Alternate, simple.

*Length.*—About 4 cm.

*Width.*—About 4.4 cm.

*Shape.*—Roughly peltate with five shallow lobes.

*Apex.*—Rounded.

*Base.*—Obtuse.

*Margin.*—Entire.

*Texture, upper surface.*—Smooth, glabrous.

*Texture, lower surface.*—Scattered pubescence.

*Venation pattern.*—Radiating from the center; reticulate.

*Color.*—Developing leaves, upper surface: Close to 137B. Developing leaves, lower surface: Close to 147B. Fully expanded leaves, upper surface: Close to 137A; venation, close to 138C. Fully expanded leaves, lower surface: Close to 138B; venation, close to 138D.

*Petioles.*—Length: About 9.3 cm. Diameter: About 1.5 mm. Texture, upper and lower surfaces: Smooth, glabrous. Color, upper and lower surfaces: Close to 145A.

Flower description:

*Flower type and habit.*—Single roughly rounded axillary flowers that face initially upright and then bending outwardly with development. Freely flowering habit, about nine to ten open flowers and flower buds per lateral branch.

*Natural flowering season.*—Long flowering period; plants flower from spring until autumn in California; flowering continuous during this period. Plants initiate flower development about four weeks after planting.

*Flower longevity on the plant.*—About three to four days; flowers persistent.

*Fragrance.*—Faint; floral-like, pleasant.

*Flowers.*—Appearance: Flowers roughly rounded with seven to eight clawed petals in a single whorl. Diameter: About 5.2 cm. Depth (length): About 3 cm.

*Flower buds.*—Length: About 1.2 cm. Diameter: About 8 mm. Shape: Roughly spherical. Color: Close to 21C.

*Corolla.*—Arrangement/appearance: Single whorl of seven to eight petals with narrow clawed bases. Total petal length: About 3.5 cm. Petal lobe length: About 2 cm. Petal lobe width: About 2.1 cm. Petal claw length: About 1.5 cm. Petal claw width: About 1 mm. Petal shape: Roughly spatulate. Petal apex: Broadly emarginate. Petal margin: Entire; fringed. Petal texture, upper and lower surfaces: Smooth, glabrous; satiny. Color: When opening, upper surface: Close to 23A. When opening, lower surface: Close to 23B. Fully opened, upper surface: Close to 21A; claw, close to 11A; color becoming close to 17B with development. Fully opened, lower surface: Close to 21B to 21C; color becoming closer to 21C with development.

*Sepals.*—Arrangement/appearance: Five in a single star-shaped whorl. Length: About 1.8 cm. Width: About 4 mm. Shape: Elliptical. Apex: Acuminate. Base: Truncate. Margin: Entire. Texture, upper and lower surfaces: Smooth, glabrous. Color, upper surface: Close to 15C. Color, lower surface: Close to 16C.

*Peduncles.*—Length: About 15 cm. Diameter: About 2 mm. Texture: Smooth, glabrous. Strength: Strong. Color: Close to 145C.

*Reproductive organs.*—Stamens: Quantity per flower: Typically seven to nine. Filament length: About 1.1 mm. Filament color: Close to 15D. Anther shape: Narrowly oblong. Anther size: About 1 mm by 4 mm. Anther color: Close to 17C. Pollen amount: Scarce. Pollen color: Close to 17A. Pistils: Quantity per flower: Typically one. Pistil length: About 9 mm. Stigma shape: Three-parted. Stigma color: Close to 15C. Style length: About 4 mm. Style color: Close to 1C. Ovary color: Close to 145D.

*Seed/fruit.*—Seed and fruit production has not been observed.

Disease/pest resistance: Plants of the new *Nasturtium* have not been noted to be resistant to pathogens and pests common to *Nasturtium*.

Temperature tolerance: Plants of the new *Nasturtium* have been observed to tolerate temperatures from about 0° C. to about 35° C.

It is claimed:

1. A new and distinct *Nasturtium* plant named 'Ahiru no Ashi' as illustrated and described.

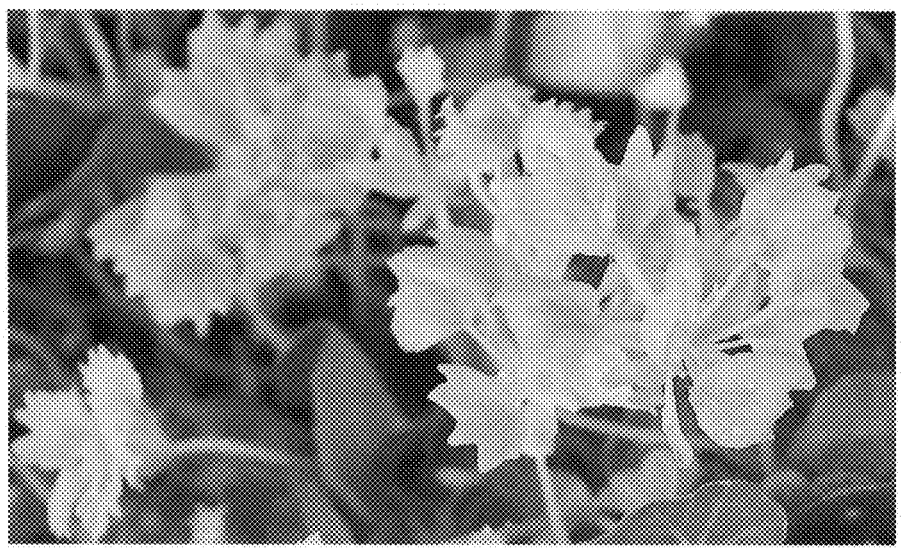
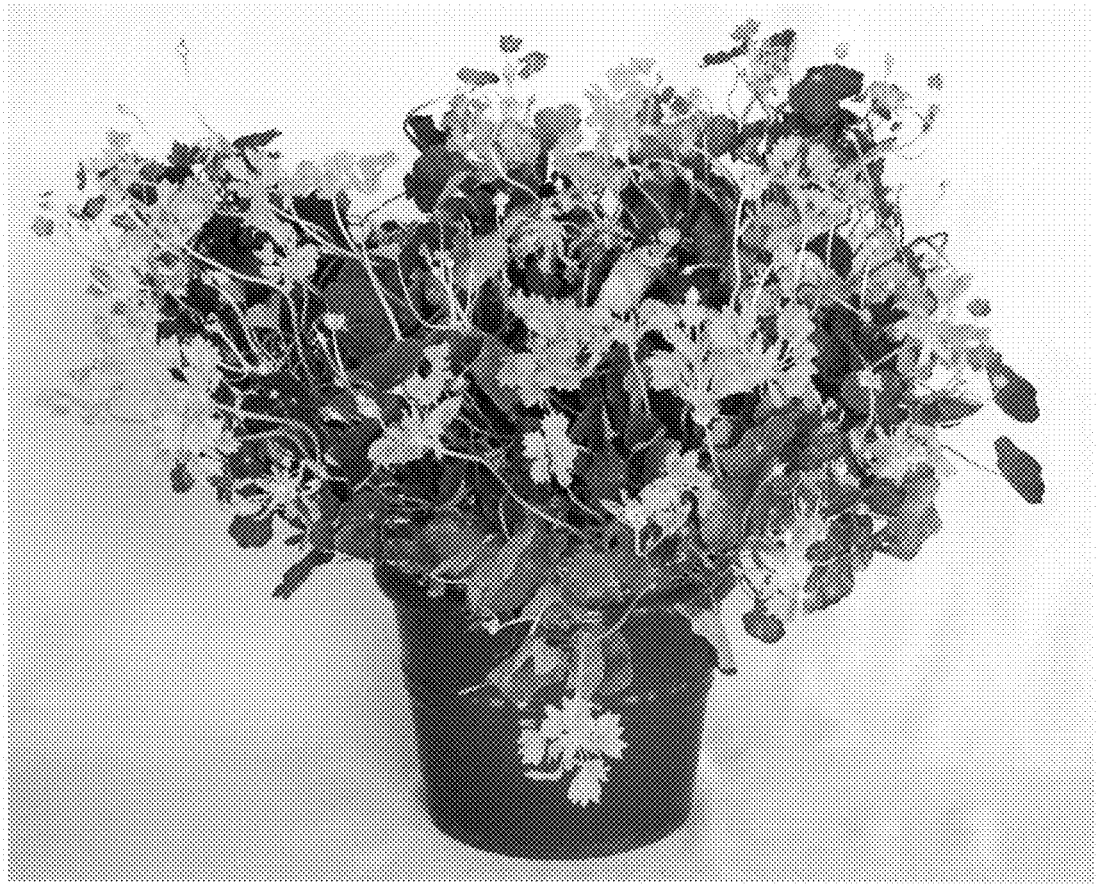

* * * * *